US 7,491,790 B2

(12) United States Patent
Bojkova et al.

(10) Patent No.: US 7,491,790 B2
(45) Date of Patent: Feb. 17, 2009

(54) SULFIDE-CONTAINING POLYTHIOLS

(75) Inventors: Nina V. Bojkova, Monroeville, PA (US); Robert A. Smith, Murrysville, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 12/037,241

(22) Filed: Feb. 26, 2008

(65) Prior Publication Data
US 2008/0161528 A1    Jul. 3, 2008

Related U.S. Application Data

(62) Division of application No. 11/233,790, filed on Sep. 23, 2005, now Pat. No. 7,411,034, which is a division of application No. 10/725,034, filed on Dec. 2, 2003, now Pat. No. 7,009,032.

(51) Int. Cl.
C08G 75/14    (2006.01)
(52) U.S. Cl. .................. 528/373; 528/374; 528/375
(58) Field of Classification Search .......... 528/373, 528/374, 375
See application file for complete search history.

(56) References Cited

U.S. PATENT DOCUMENTS

| | | | |
|---|---|---|---|
| 2,327,966 A * | 8/1943 | Morey .................. 568/42 |
| 2,370,567 A | 2/1945 | Muskat et al. | |
| 2,403,113 A | 7/1946 | Muskat et al. | |
| 2,644,007 A | 6/1953 | Irwin | |
| 2,680,127 A | 6/1954 | Slocombe et al. | |
| 2,908,703 A | 10/1959 | Latourette et al. | |
| 2,965,650 A | 12/1960 | Howard, Jr. | |
| 2,965,651 A | 12/1960 | Kosmin | |
| 3,169,945 A | 2/1965 | Hostettler et al. | |
| 3,361,706 A | 1/1968 | Meriwether et al. | |
| 3,562,172 A | 2/1971 | Ono et al. | |
| 3,567,605 A | 3/1971 | Becker | |
| 3,578,602 A | 5/1971 | Ono et al. | |
| 3,766,148 A | 10/1973 | Taub | |
| 3,866,242 A | 2/1975 | Slagel | |
| 3,971,892 A | 7/1976 | Schlichte | |
| 4,095,637 A | 6/1978 | Krishnan | |
| 4,101,529 A | 7/1978 | Ammons | |
| 4,153,777 A | 5/1979 | Slagel | |
| 4,160,853 A | 7/1979 | Ammons | |
| 4,166,043 A | 8/1979 | Uhlmann et al. | |
| 4,208,507 A | 6/1980 | Stutz et al. | |
| 4,215,010 A | 7/1980 | Hovey et al. | |
| 4,342,668 A | 8/1982 | Hovey et al. | |
| 4,365,051 A | 12/1982 | Chung et al. | |
| 4,367,170 A | 1/1983 | Uhlmann et al. | |
| 4,556,605 A | 12/1985 | Mogami et al. | |
| 4,581,433 A | 4/1986 | Potter et al. | |
| 4,637,698 A | 1/1987 | Kwak et al. | |
| 4,719,296 A | 1/1988 | Irie et al. | |
| 4,720,356 A | 1/1988 | Chu | |
| 4,731,264 A | 3/1988 | Lin et al. | |
| 4,756,973 A | 7/1988 | Sakagami et al. | |
| 4,764,430 A | 8/1988 | Blackburn et al. | |
| 4,798,745 A | 1/1989 | Martz et al. | |
| 4,798,746 A | 1/1989 | Claar et al. | |
| 4,808,690 A | 2/1989 | Slagel | |
| 4,810,812 A | 3/1989 | Matsuda et al. | |
| 4,816,584 A | 3/1989 | Kwak et al. | |
| 4,818,096 A | 4/1989 | Heller et al. | |
| 4,826,977 A | 5/1989 | Heller et al. | |
| 4,856,857 A | 8/1989 | Takeuchi et al. | |
| 4,866,103 A | 9/1989 | Cassidy et al. | |
| 4,873,027 A | 10/1989 | Umemoto et al. | |
| 4,880,667 A | 11/1989 | Welch et al. | |
| 4,889,413 A | 12/1989 | Ormsby et al. | |
| 4,892,920 A | 1/1990 | Quay et al. | |
| 4,904,525 A | 2/1990 | Taniguchi et al. | |
| 4,931,219 A | 6/1990 | Kwiatkowski et al. | |
| 4,931,220 A | 6/1990 | Haynes et al. | |
| 5,066,818 A | 11/1991 | Gemert et al. | |
| 5,071,951 A | 12/1991 | Ulrich et al. | |
| 5,104,692 A | 4/1992 | Belmares | |
| 5,128,433 A | 7/1992 | Lecompte et al. | |
| 5,134,191 A | 7/1992 | Takarada et al. | |
| 5,158,922 A | 10/1992 | Hinney et al. | |
| 5,166,345 A | 11/1992 | Akashi et al. | |
| 5,196,485 A | 3/1993 | McMonigal et al. | |
| 5,225,472 A | 7/1993 | Cameron et al. | |
| 5,231,156 A | 7/1993 | Lin | |
| 5,236,958 A | 8/1993 | Miyashita | |
| 5,236,978 A | 8/1993 | Selvig et al. | |
| 5,238,931 A | 8/1993 | Yoshikawa et al. | |
| 5,239,012 A | 8/1993 | McEntire et al. | |
| 5,252,742 A | 10/1993 | Miyashita | |
| 5,256,452 A | 10/1993 | McMonigal | |
| 5,274,132 A | 12/1993 | Van Gemert | |
| 5,310,577 A | 5/1994 | Mase et al. | |
| 5,323,191 A | 6/1994 | Firtion et al. | |
| 5,352,758 A | 10/1994 | Kanemura et al. | |
| 5,359,035 A | 10/1994 | Habermann | |
| 5,359,085 A | 10/1994 | Iwamoto et al. | |

(Continued)

FOREIGN PATENT DOCUMENTS

DE    116520    11/1975

(Continued)

OTHER PUBLICATIONS

Ullmann's Encyclopedia of Industrial Chemistry, 5th Edition, 1992, vol. A21, pp. 673-674.

*Primary Examiner*—Kuo-Liang Peng
(74) *Attorney, Agent, or Firm*—Deborah M. Altman

(57) ABSTRACT

The present invention relates to sulfide-containing polythiols and their methods of preparation. Sulfide-containing polythiols can have a variety of uses and applications. The sulfide-containing polythiols of the present invention can be especially useful in polyurethane compositions for the manufacture of ophthalmic lenses.

1 Claim, No Drawings

U.S. PATENT DOCUMENTS

| | | | |
|---|---|---|---|
| 5,373,033 A | 12/1994 | Toh et al. | |
| 5,384,077 A | 1/1995 | Knowles | |
| 5,384,379 A | 1/1995 | Bader et al. | |
| 5,391,327 A | 2/1995 | Ligas et al. | |
| 5,405,958 A | 4/1995 | Van Gemert | |
| 5,429,774 A | 7/1995 | Kumar | |
| 5,462,806 A | 10/1995 | Konishi et al. | |
| 5,466,398 A | 11/1995 | Van Gemert | |
| 5,470,813 A | 11/1995 | Le-Khac | |
| 5,482,908 A | 1/1996 | Le-Khac | |
| 5,488,119 A | 1/1996 | Fischer-Reimann et al. | |
| 5,496,641 A | 3/1996 | Mase et al. | |
| 5,498,686 A | 3/1996 | Effer et al. | |
| 5,552,091 A | 9/1996 | Kumar | |
| 5,602,198 A | 2/1997 | Das et al. | |
| 5,618,586 A | 4/1997 | Swarup et al. | |
| 5,621,017 A | 4/1997 | Kobayakawa et al. | |
| 5,631,339 A | 5/1997 | Faler et al. | |
| 5,645,767 A | 7/1997 | Van Gemert | |
| 5,646,230 A | 7/1997 | Pantone et al. | |
| 5,658,501 A | 8/1997 | Kumar et al. | |
| 5,663,244 A | 9/1997 | Barancyk et al. | |
| 5,679,756 A | 10/1997 | Zhu et al. | |
| 5,684,083 A | 11/1997 | Temple et al. | |
| 5,693,738 A | 12/1997 | Okazaki et al. | |
| 5,698,141 A | 12/1997 | Kumar | |
| 5,739,243 A | 4/1998 | Herold et al. | |
| 5,753,146 A | 5/1998 | Van Gemert et al. | |
| 5,770,115 A | 6/1998 | Misura | |
| 5,776,376 A | 7/1998 | Nagoh et al. | |
| 5,807,975 A | 9/1998 | Amagai et al. | |
| 5,811,503 A | 9/1998 | Herold et al. | |
| 5,811,506 A | 9/1998 | Slagel | |
| 5,814,410 A | 9/1998 | Singer et al. | |
| 5,821,287 A | 10/1998 | Hu et al. | |
| 5,830,578 A | 11/1998 | Ono et al. | |
| 5,910,522 A | 6/1999 | Schmidt et al. | |
| 5,917,006 A | 6/1999 | Smith et al. | |
| 5,932,681 A | 8/1999 | Herold et al. | |
| 5,942,158 A | 8/1999 | Okoroafor et al. | |
| 5,945,504 A | 8/1999 | Amagi et al. | |
| 5,961,889 A | 10/1999 | Jiang et al. | |
| 5,962,617 A | 10/1999 | Slagel | |
| 5,962,619 A | 10/1999 | Seneker et al. | |
| 5,976,422 A | 11/1999 | Okoroafor et al. | |
| 5,976,701 A | 11/1999 | Barancyk et al. | |
| 6,025,026 A | 2/2000 | Smith et al. | |
| 6,042,737 A | 3/2000 | Basil et al. | |
| 6,060,001 A | 5/2000 | Welch et al. | |
| 6,083,427 A | 7/2000 | Henry | |
| 6,100,362 A | 8/2000 | Okazaki et al. | |
| 6,113,814 A | 9/2000 | Gemert et al. | |
| 6,127,505 A | 10/2000 | Slagel | |
| 6,130,307 A | 10/2000 | Amagai et al. | |
| 6,150,430 A | 11/2000 | Walters et al. | |
| 6,153,126 A | 11/2000 | Kumar | |
| 6,166,129 A | 12/2000 | Yosthauser et al. | |
| 6,174,984 B1 | 1/2001 | Peter | |
| 6,175,450 B1 | 1/2001 | Andreani et al. | |
| 6,187,444 B1 | 2/2001 | Bowles, III et al. | |
| 6,268,055 B1 | 7/2001 | Walters et al. | |
| 6,296,785 B1 | 10/2001 | Nelson et al. | |
| 6,342,571 B1 | 1/2002 | Smith et al. | |
| 6,348,604 B1 | 2/2002 | Nelson et al. | |
| 6,353,039 B1 | 3/2002 | Rheinberger et al. | |
| 6,353,102 B1 | 3/2002 | Kumar | |
| 6,432,526 B1 | 8/2002 | Arney | |
| 6,432,544 B1 | 8/2002 | Stewart et al. | |
| 6,433,043 B1 | 8/2002 | Misura et al. | |
| 6,436,525 B1 | 8/2002 | Welch et al. | |
| 6,441,119 B1 | 8/2002 | Kosaka | |
| 6,472,495 B1 | 10/2002 | Yoshimura et al. | |
| 6,506,488 B1 | 1/2003 | Stewart et al. | |
| 6,509,418 B1 | 1/2003 | Zook et al. | |
| 6,531,076 B2 | 3/2003 | Crano et al. | |
| 6,555,028 B2 | 4/2003 | Walters et al. | |
| 6,602,603 B2 | 8/2003 | Welch et al. | |
| 6,631,021 B2 | 10/2003 | Smith et al. | |
| 6,733,887 B2 | 5/2004 | Okoroafor et al. | |
| 7,009,032 B2 | 3/2006 | Bojkova et al. | |
| 7,144,969 B2 | 12/2006 | McDonald | |
| 7,169,375 B2 | 1/2007 | Chisholm | |
| 2001/0047043 A1 | 11/2001 | Okoroafor et al. | |
| 2003/0096935 A1 | 5/2003 | Nagpal et al. | |
| 2003/0144452 A1 | 7/2003 | Jallouli et al. | |
| 2003/0149217 A1 | 8/2003 | Bojkova et al. | |
| 2004/0138401 A1 | 7/2004 | Bojkova et al. | |
| 2006/0008596 A1 | 1/2006 | Pokorny et al. | |
| 2006/0025563 A1 | 2/2006 | Bojkova et al. | |

FOREIGN PATENT DOCUMENTS

| | | |
|---|---|---|
| DE | 3201224 C2 | 9/1989 |
| EP | 0 116 735 A1 | 8/1984 |
| EP | 0 802 208 A1 | 4/1987 |
| EP | 0 146 136 B1 | 5/1990 |
| EP | 0 454 066 A2 | 10/1991 |
| EP | 0 578 220 A2 | 1/1994 |
| EP | 0 294 056 B1 | 4/1994 |
| EP | 0 329 387 B1 | 6/1994 |
| EP | 0 780 413 A1 | 6/1997 |
| EP | 0 802 208 B1 | 10/1997 |
| EP | 0 936 233 A2 | 8/1999 |
| EP | 1 099 721 A1 | 5/2001 |
| EP | 1 134 242 A2 | 9/2001 |
| EP | 1 197 505 A1 | 4/2002 |
| EP | 0 927 730 B1 | 9/2003 |
| EP | 1 384 736 A1 | 1/2004 |
| FR | 2 751 763 A1 | 1/1998 |
| GB | 1 419 985 | 1/1976 |
| GB | 150 1801 | 2/1978 |
| JP | 62-226134 | 5/1987 |
| JP | 62-195383 | 8/1987 |
| JP | 63-178193 | 7/1988 |
| JP | 3-2864 | 1/1991 |
| JP | 3-35236 | 2/1991 |
| JP | 3-269507 | 12/1991 |
| JP | 5-28753 | 4/1993 |
| JP | 2000-256435 | 9/2000 |
| WO | WO 96/11926 | 4/1996 |
| WO | WO 96/18926 | 6/1996 |
| WO | WO 96/19741 | 6/1996 |
| WO | WO 96/37573 | 11/1996 |
| WO | WO 97/00910 | 1/1997 |
| WO | WO 97/03373 | 1/1997 |
| WO | WO 97/05213 | 2/1997 |
| WO | WO 97/06944 | 2/1997 |
| WO | WO 97/21122 | 6/1997 |
| WO | WO 98/37115 | 8/1998 |
| WO | WO 99/29791 | 6/1999 |
| WO | WO 00/14137 | 3/2000 |
| WO | WO 00/17249 | 3/2000 |
| WO | WO 0024449 | 5/2000 |
| WO | WO 01/36507 A1 | 5/2001 |
| WO | WO 01/36508 A1 | 5/2001 |
| WO | WO 01/66623 A1 | 9/2001 |
| WO | WO 03/011925 | 2/2003 |
| WO | WO 03/042270 A1 | 5/2003 |
| WO | WO 03/044070 A1 | 5/2003 |
| WO | WO 2004/060951 A1 | 7/2004 |
| WO | WO 2004/060971 A2 | 7/2004 |
| WO | WO 2006/130339 A1 | 12/2006 |

\* cited by examiner

SULFIDE-CONTAINING POLYTHIOLS

This application is a division of U.S. patent application Ser. No. 11/233,790 filed Sep. 23, 2005, which is a division of U.S. patent application Ser. No. 10/725,034 filed Dec. 2, 2003, now issued as U.S. Pat. No. 7,009,032 B2, which claims the benefit of priority from Provisional Patent Application No. 60/435,537 filed on Dec. 20, 2002.

The present invention relates to sulfide containing polythiols and methods for their preparation. Sulfide-containing polythiols can have a variety of uses and applications. The sulfide-containing polythiols of the present invention can be especially useful in polyurethane compositions for the manufacture of ophthalmic lenses.

For the purposes of this specification, unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The present invention provides for a composition comprising one or more sulfide-containing polythiols chosen from the materials represented by the following structural formulas:

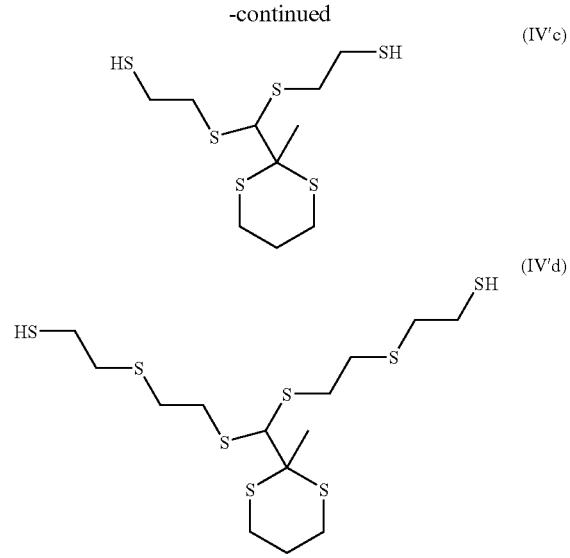

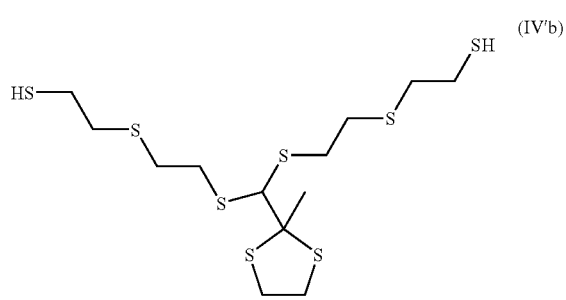

and methods for their preparation.

The present invention further provides for a composition comprising a sulfide-containing oligomeric polythiol represented by the following structural formula:

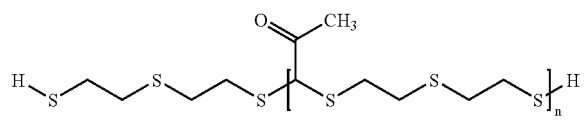

wherein n can represent an integer from 1 to 20, and method for its preparation.

In a non-limiting embodiment, the sulfide-containing polythiols of the present invention can comprise 1,3-dithiolane and 1,3-dithiane. Non-limiting examples of sulfide-containing polythiols comprising 1,3-dithiolane can include the materials represented by structural formulas IV'a and b, above. Non-limiting examples of sulfide-containing polythiols comprising 1,3-dithiane can include the materials represented by structural formulas IV'c and d, above.

The sulfide-containing polythiols comprising 1,3-dithiolane or 1,3-dithiane can be prepared by reacting asym-dichloroacetone with polymercaptan, and then reacting the reaction product with polymercaptoalkylsulfide, polymercaptan or mixtures thereof.

Non-limiting examples of suitable polymercaptans for use in the reaction with asym-dichloroacetone can include but are not limited to materials represented by the following formula,

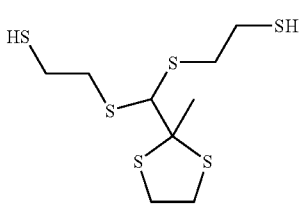

wherein Y can represent $CH_2$ or $(CH_2-S-CH_2)$, and n can be an integer from 0 to 5. In a non-limiting embodiment, the polymercaptan for reaction with asym-dichloroacetone in the present invention can be chosen from ethanedithiol, propanedithiol, and mixtures thereof.

The amount of asym-dichloroacetone and polymercaptan suitable for carrying out the above reaction can vary. In a non-limiting embodiment, asym-dichloroacetone and polymercaptan can be present in the reaction mixture in an amount such that the molar ratio of dichloroacetone to polymercaptan can be from 1:1 to 1:10.

Suitable temperatures for reacting asym-dichloroacetone with polymercaptane can vary. In a non-limiting embodiment, the reaction of asym-dichloroacetone with polymercaptane can be carried out at a temperature within the range of from 0 to 100° C.

Non-limiting examples of suitable polymercaptans for use in the reaction with the reaction product of the asym-dichloroacetone and polymercaptan, can include but are not limited to materials represented by the above structural formula 1, aromatic polymercaptans, cycloalkyl polymercaptans, heterocyclic polymercaptans, branched polymercaptans, and mixtures thereof.

Non-limiting examples of suitable polymercaptoalkylsulfides for use in the reaction with the reaction product of the asym-dichloroacetone and polymercaptan, can include but are not limited to materials represented by the following formula,

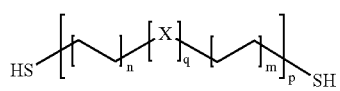

2 wherein X can represent O, S or Se, n can be an integer from 0 to 10, m can be an integer from 0 to 10, p can be an integer from 1 to 10, q can be an integer from 0 to 3, and with the proviso that (m+n) is an integer from 1 to 20.

Non-limiting examples of suitable polymercaptoalkylsulfides for use in the present invention can include branched polymercaptoalkylsulfides. In a non-limiting embodiment, the polymercaptoalkylsulfide for use in the present invention can be dimercaptoethylsulfide.

The amount of polymercaptan, polymercaptoalkylsulfide, or mixtures thereof, suitable for reacting with the reaction product of asym-dichloroacetone and polymercaptan, can vary. In a non-limiting embodiment, polymercaptan, polymercaptoalkylsulfide, or a mixture thereof, can be present in the reaction mixture in an amount such that the equivalent ratio of reaction product to polymercaptan, polymercaptoalkylsulfide, or a mixture thereof, can be from 1:1.01 to 1:2. Moreover, suitable temperatures for carrying out this reaction can vary. In a non-limiting embodiment, the reaction of polymercaptan, polymercaptoalkylsulfide, or a mixture thereof, with the reaction product can be carried out at a temperature within the range of from 0 to 100° C.

In a non-limiting embodiment, the reaction of asym-dichloroacetone with polymercaptan can be carried out in the presence of an acid catalyst. The acid catalyst can be selected from a wide variety known in the art, such as but not limited to Lewis acids and Bronsted acids. Non-limiting examples of suitable acid catalysts can include those described in Ullmann's Encyclopedia of Industrial Chemistry, 5$^{th}$ Edition, 1992, Volume A21, pp. 673 to 674. In further alternate non-limiting embodiments, the acid catalyst can be chosen from boron trifluoride etherate, hydrogen chloride, toluenesulfonic acid, and mixtures thereof.

The amount of acid catalyst can vary. In a non-limiting embodiment, a suitable amount of acid catalyst can be from 0.01 to 10 percent by weight of the reaction mixture.

In another non-limiting embodiment, the reaction product of asym-dichloroacetone and polymercaptan can be reacted with polymercaptoalkylsulfide, polymercaptan or mixtures thereof, in the presence of a base. The base can be selected from a wide variety known in the art, such as but not limited to Lewis bases and Bronsted bases. Non-limiting examples of suitable bases can include those described in Ullmann's Encyclopedia of Industrial Chemistry, 5$^{th}$ Edition, 1992, Volume A21, pp. 673 to 674. In a further non-limiting embodiment, the base can be sodium hydroxide.

The amount of base can vary. In a non-limiting embodiment, a suitable equivalent ratio of base to reaction product of the first reaction, can be from 1:1 to 10:1.

In another non-limiting embodiment, the preparation of these sulfide-containing polythiols can include the use of a solvent. The solvent can be selected from a wide variety known in the art.

In a further non-limiting embodiment, the reaction of asym-dichloroacetone with polymercaptan can be carried out in the presence of a solvent. The solvent can be selected from a wide variety of known materials. In a non-limiting embodiment, the solvent can be selected from but is not limited to organic solvents, including organic inert solvents. Non-limiting examples of suitable solvents can include but are not limited to chloroform, dichloromethane, 1,2-dichloroethane, diethyl ether, benzene, toluene, acetic acid and mixtures thereof. In still a further embodiment, the reaction of asym-dichloroacetone with polymercaptan can be carried out in the presence of toluene as solvent.

In another embodiment, the reaction product of asym-dichloracetone and polymercaptan can be reacted with polymercaptoalkylsulfide, polymercaptan or mixtures thereof, in the presence of a solvent, wherein the solvent can be selected from but is not limited to organic solvents including organic inert solvents. Non-limiting examples of suitable organic and inert solvents can include alcohols such as but not limited to methanol, ethanol and propanol; aromatic hydrocarbon solvents such as but not limited to benzene, toluene, xylene; ketones such as but not limited to methyl ethyl ketone; water and mixtures thereof. In a further non-limiting embodiment, this reaction can be carried out in the presence of a mixture of toluene and water as solvent system. In another non-limiting embodiment, this reaction can be carried out in the presence of ethanol as solvent.

The amount of solvent can widely vary. In a non-limiting embodiment, a suitable amount of solvent can be from 0 to 99 percent by weight of the reaction mixture. In a further non-limiting embodiment, the reaction can be carried out neat; that is without solvent.

In another non-limiting embodiment, the reaction of asym-dichloroacetone with polyercaptan can be carried out in the presence of a dehydrating reagent. The dehydrating reagent can be selected from a wide variety known in the art. Suitable dehydrating reagents for use in this reaction can include but are not limited to magnesium sulfate. The amount of dehydrating reagent can vary widely according to the stoichiometry of the dehydrating reaction.

In a non-limiting embodiment, 1,1-dichloroacetone can be introduced together with 1,2-ethanedithiol in the presence of an acid catalyst to produce 2-methyl-2-dichloromethyl-1,3-dithiolane, as shown below.

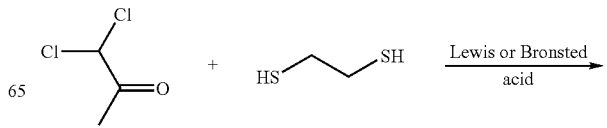

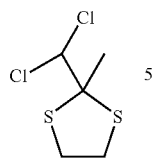

In a further non-limiting embodiment, 1,1-dichloroacetone can be introduced together with 1,3-propanedithiol in the presence of an acid catalyst to produce 2-methyl-2-dichloromethyl-1,3-dithiane, as shown below.

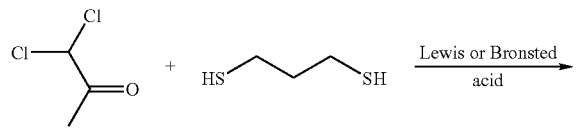

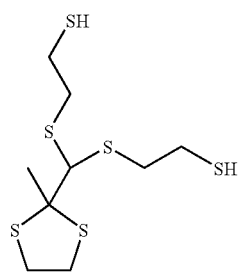

In another non-limiting embodiment, 2-methyl-2-dichloromethyl-1,3-dithiolane can be introduced together with dimercaptoethylsulfide in the presence of a base to produce a dimercapto 1,3-dithiolane polythiol of the present invention, as shown below.

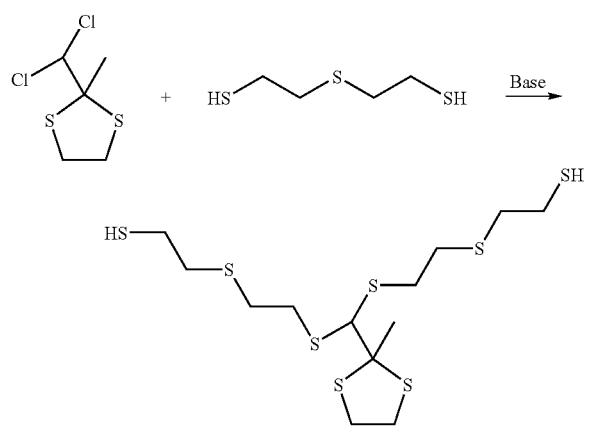

In another non-limiting embodiment, 2-methyl-2-dichloromethyl-1,3-dithiolane can be introduced together with 1,2-ethanedithiol in the presence of a base to produce a dimercapto 1,3-dithiolane polythiol of the present invention, as shown below.

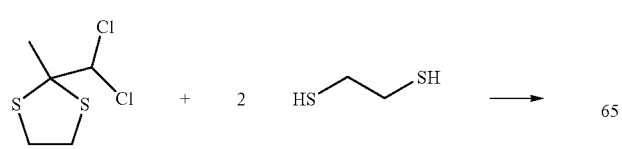

In another non-limiting embodiment, 2-methyl-2-dichloromethyl-1,3-dithiane can be introduced together with dimercaptoethylsulfide in the presence of a base to produce a dimercapto 1,3-dithiane polythiol of the present invention as shown below.

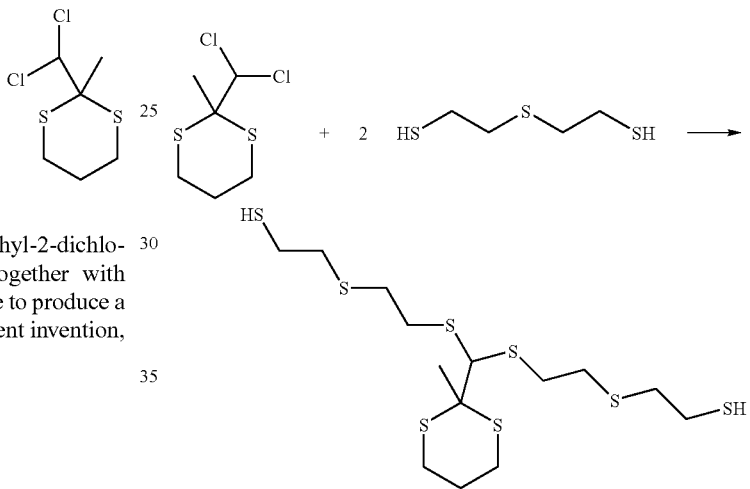

In another non-limiting embodiment, 2-methyl-2-dichloromethyl-1,3-dithiane can be introduced together with 1,2-ethanedithiol in the presence of a base to produce a dimercapto 1,3-dithiane polythiol of the present invention as shown below.

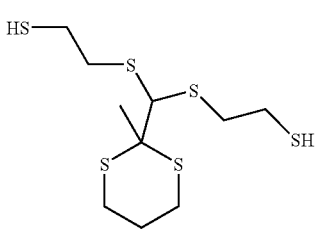

In another non-limiting embodiment of the present invention, a sulfide-containing oligomeric polythiol of the following structural formula

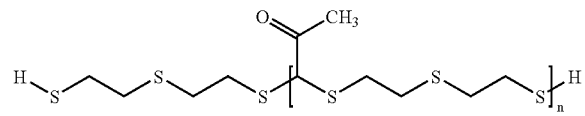

wherein n can be an integer from 1 to 20, can be prepared by introducing asym-dichloroacetone together with polymercaptoalkylsulfide, in the presence of a base.

Non-limiting examples of suitable polymercaptoalkylsulfides for use in this reaction can include but are not limited to those materials represented by general formula 2 as previously recited herein.

Further non-limiting examples of suitable polymercaptoalkylsulfides for use in the present invention can include branched polymercaptoalkylsulfides. In a non-limiting embodiment, the polymercaptoalkylsulfide can be dimercaptoethylsulfide.

Suitable bases for use in this reaction can include those previously recited herein.

In another non-limiting embodiment, the reaction of asym-dichloroacetone with polymercaptoalkylsulfide can be carried out in the presence of a phase transfer catalyst. Suitable phase transfer catalysts for use in the present invention are known and varied. Non-limiting examples can include but are not limited to tetraalkylammonium salts and tetraalkylphosphonium salts. In a further non-limiting embodiment, this reaction can be carried out in the presence of tetrabutylphosphonium bromide as phase transfer catalyst. The amount of phase transfer catalyst can vary widely. In a non-limiting embodiment, the amount of phase transfer catalyst can be from 0 to 50 equivalent percent, or from 0 to 10 equivalent percent, or from 0 to 5 equivalent percent, to the polymercaptosulfide reactants.

In another non-limiting embodiment, the preparation of the polythioether oligomeric dithiol of the present invention can include the use of solvent. Non-limiting examples of suitable solvents can include those previously recited herein.

In a non-limiting embodiment, "n" moles of 1,1-dichloroacetone can be reacted with "n+1" moles of polymercaptoethylsulfide wherein n can represent an integer of from 1 to 20, to produce the polythioether oligomeric dithiol of the invention as follows.

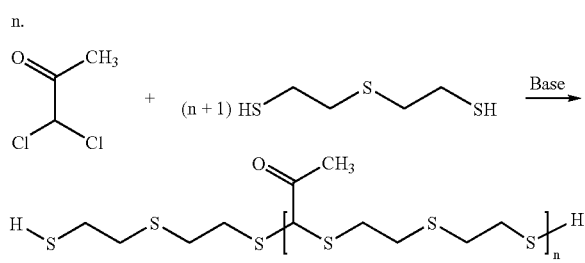

In a non-limiting embodiment, the polythiols of the present invention can be suitable for optical or ophthalmic applications.

The invention has been described with reference to non-limiting embodiments. Obvious modifications and alterations can occur to others upon reading and understanding the detailed description.

EXAMPLES

Example 1

Synthesis of
2-Methyl-2-Dichloromethyl-1,3-Dithiolane

In a three-necked flask equipped with a magnetic stirrer and having a nitrogen blanket at the inlet and outlet, were added 13.27 grams (0.106 mole) of 1,1-dichloroacetone, 11.23 grams (0.119 mole) of 1,2-ethanedithiol, 20 grams of anhydrous MgSO4, and 5 grams of Montmorilonite K-10 (obtained from Aldrich Chemical) in 200 ml of toluene. This reaction mixture was stirred for 24 hours at room temperature. The insoluble material was filtered off and the toluene was evaporated under vacuum using a Buchi Rotaevaporator, to provide 17.2 grams (80% yield) of 2-methyl-2-dichloromethyl-1,3-dithiolane. The product was then vacuum distilled at a temperature within the range of from 102 to 112° C., at a pressure of 12 mm Hg. An NMR analysis was then conducted using Varian Unity Plus Machine. The NMR results are as follows: $^1$H NMR (CDCL$_3$, 200 MHz): 5.93 (s, 1H); 3.34 (s, 4H); 2.02 (s, 3H); $^{13}$C NMR (CDCl$_3$, 50 MHz) : 80.57; 40.98; 25.67.

Example 2

(Paper Example only; Example was Not Actually Conducted)

Synthesis of
2-Methyl-2-Dichloromethyl-1,3-Dithiane

In a three-necked flask equipped with a magnetic stirrer and having a nitrogen blanket at the inlet and outlet, are added 13.97 grams (0.11 mole) of 1,1-dichloroacetone, 10.8 grams (0.10 mole) of 1,3-propanedithiol and 50 milliliters of chloroform. The reaction mixture is cooled to 0° C. A slow steam of hydrogen chloride gas is then bubbled through the solution for approximately five minutes. Upon the reaction mixture reaching saturation, the mixture is allowed to set at room temperature for approximately thirty minutes. The solvent is then evaporated and a crude 2-methyl-2-dichloromethyl-1,3-dithiane derivative is expected in a yield of approximately 80-90%.

Example 3

(Paper Example only; Example was Not Actually Conducted)

Reaction of
2-Methyl-2-Dichloromethyl-1,3-Dithiolane with
2-Mercaptoethyl Sulfide In a three-necked flask equipped with a magnetic stirrer and having a nitrogen blanket at the inlet and outlet, is added 20.30 grams (0.1 mole) of 2-methyl-2-dichloromethyl-1,3-dithiolane, 30.86 grams (0.2 mole) of 2-mercaptoethylsulfide, and 100 milliliters of ethanol. The 2-methyl-2-dichloromethyl-1,3-dithiolane is prepared as described in Example 1 above. To this reaction mixture is added dropwise 16.3 grams (0.2 mol) of 49% sodium hydroxide (NaOH) at a temperature of from 35-40° C. The temperature is then raised to 50° C. and the reaction mixture is allowed to set at 50° C. for two hours. The mixture is then cooled to room temperature and the precipitated sodium chloride (NaCl) is removed by filtration. The ethanol and water are evaporated under vacuum to obtain the dimercapto polysulfide in an expected yield of approximately 60-70%.

Example 4

Synthesis of Oligomeric Polythioether Dithiol (PTE Dithiol 1) wherein n=1

Dissolved in 350 ml of $H_2O$ was 44.15 grams (1.01 mol) of NaOH. This solution was cooled to room temperature, and 500 ml of toluene was added, followed by the addition of 159.70 grams (1.04 mol) of dimercaptoethylsulfide. The mixture was warmed to 40° C., stirred and cooled to room temperature. Added drop-wise to the mixture was 66.35 grams (0.52 mol) of 1,1-dichloroacetone dissolved in 250 ml of toluene. The mixture was stirred for an additional 20 hours at room temperature. The temperature of the mixture was maintained between 20-25 C. The organic phase was separated, washed with 2×100 ml of H2O, 1×100 ml of brine and dried over anhydrous $MgSO_4$. The drying agent was filtered off and toluene was evaporated using a Buchi Rotaevaporator. The hazy residue was filtered through Celite to produce 182 grams (i.e., 96% yield) of PTE Dithiol, as a colorless clear oily liquid.

A Mass Spectra was conducted on a product sample using a Mariner Bio Systems apparatus. The results were as follows: ESI-MS: 385 (M+Na). Therefore, the molecular weight was 362.

A NMR was conducted on a product sample using a Varian Unity Plus machine. The results were as follows: $^1$H NMR ($CDCl_3$, 200 MHz): 4.56 (s, 1H), 2.75 (m, 16H), 2.38 (s, 3H), 1.75 (m, 1.5H)).

The SH groups within the product were determined using the following procedure. A sample size (0.1 mg) of the product was combined with 50 mL of tetrahydrofuran (THF)/propylene glycol (80/20) and stirred at room temperature until the sample was substantially dissolved. While stirring, 25.0 mL of 0.1 N iodine solution (which was commercially obtained from Aldrich 31, 8898-1) was added to the mixture and then allowed to react for a time period of from 5 to 10 minutes. To this mixture was added 2.0 mL concentrated HCl. The mixture was then titrated potentiometrically with 0.1 N sodium thiosulfate in the millivolt (mV) mode. A blank value was initially obtained by titrating 25.0 mL of iodine (including 1 mL of concentrated hydrochloric acid) with sodium thiosulfate in the same manner as conducted with the product sample.

$$\% \; SH = \frac{mLsBlank - mLSSample) \; (\text{Normality Na}2S203) \; (3.307)}{\text{sample weight, g}}$$

The following results were obtained: 13.4% SH

The refractive index (e-line) and the Abbe number were measured using a multiple wavelength Abbe Refractometer Model No. DR-M2, manufactured by ATAGO Co., Limited, in accordance with ASTM 542-00. The refractive index was 1.618 (20° C.) and the Abbe number was 35.

Example 5

Synthesis of Oligomeric Polythioether Dithiol (PTE Dithiol 2) wherein n=3

NaOH (23.4 g, 0.58 mol) was dissolved in 54 ml of $H_2O$. The solution was cooled down to room temperature and dimercaptoethylsulfide (30.8 g, 0.20 mol) was added. Upon stirring the mixture, dichloroacetone (19.0 g, 0.15 mol) was added dropwise while the temperature was maintained at from 20-25° C. After the addition of dichloroacetone was completed, the mixture was stirred for an additional 2 hours at room temperature. The mixture was acidified with 10% HCl to a pH<9, and 100 ml of dichloromethane were then added, and the mixture was stirred. Following phase separation, the organic phase was washed with 100 ml of $H_2O$, and dried over anhydrous $MgSO_4$. The drying agent was filtered off and the solvent was evaporated using a Buchi Rotaevaporator, which provided 35 grams (90%) of viscous, transparent liquid having a viscosity (73° C.) of 38 cP. The refractive index, Abbe number and SH groups were measured as recited in Example 4 to provide the following results: refractive index (e-line) of 1.622 (20° C.), Abbe number of 36, SH group analysis of 8.10%.

The invention claimed is:

1. A composition comprising at least one sulfide-containing oligomeric polythiol chosen from materials represented by the following structural formulas:

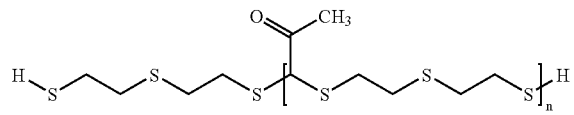

wherein n represents an integer from 1 to 20.

* * * * *